United States Patent
Li et al.

(10) Patent No.: US 9,353,045 B2
(45) Date of Patent: May 31, 2016

(54) PROCESS FOR PREPARING CHOLINE HYDROXIDE FROM TRIMETHYLAMINE AND ETHYLENE OXIDE

(71) Applicant: Dow AgroSciences LLC, Indianapolis, IN (US)

(72) Inventors: Ruokang Li, Pearland, TX (US); Ravindra S. Dixit, Lake Jackson, TX (US); Avani M. Patel, Midland, MI (US); Xiaoyun Chen, Midland, MI (US); Randy J. Pell, Midland, MI (US); John G. Pendergast, Jr., Lake Jackson, TX (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 13/743,616

(22) Filed: Jan. 17, 2013

(65) Prior Publication Data

US 2013/0190534 A1 Jul. 25, 2013

Related U.S. Application Data

(60) Provisional application No. 61/588,234, filed on Jan. 19, 2012, provisional application No. 61/720,711, filed on Oct. 31, 2012.

(51) Int. Cl.
*C07C 213/04* (2006.01)

(52) U.S. Cl.
CPC .................................. *C07C 213/04* (2013.01)

(58) Field of Classification Search
None
See application file for complete search history.

(56) References Cited

U.S. PATENT DOCUMENTS

| | | |
|---|---|---|
| 2,774,759 A | 12/1956 | Blackett et al. |
| 3,872,170 A | 3/1975 | Bosche et al. |
| 5,618,978 A | 4/1997 | Hyoda et al. |
| 2007/0193708 A1 | 8/2007 | Broucek et al. |

*Primary Examiner* — Clinton Brooks
*Assistant Examiner* — Jennifer C Sawyer
(74) *Attorney, Agent, or Firm* — Michael J. Terapane

(57) ABSTRACT

Processes for preparing N,N,N-trimethylethanolammonium hydroxide (choline hydroxide) and the choline hydroxide produced are described. These processes minimize the production of byproduct mono-ethoxylated and di-ethyoxylated choline in the product choline hydroxide. The processes generally include feeding ethylene oxide, trimethylamine, and water into a first reactor to create a first reactor product under temperature controlled conditions. The product of the first reactor is fed into a second reactor to form a second reactor product under uncontrolled, adiabatic, conditions. Finally, any unreacted trimethylamine in the second reactor product is removed to form a final product comprising choline hydroxide. Additional reactors can be used for the ethylene oxide and trimethylamine reaction.

22 Claims, 3 Drawing Sheets

PROCESS FOR PREPARING CHOLINE HYDROXIDE FROM TRIMETHYLAMINE AND ETHYLENE OXIDE

This application claims the benefit of U.S. Provisional Patent Application Ser. No. 61/588,234, filed Jan. 19, 2012, and U.S. Provisional Patent Application Ser. No. 61/720,711, filed Oct. 31, 2012.

BACKGROUND

Choline hydroxide can be produced by the reaction of trimethylamine (TMA), ethylene oxide (EO), and water. Impurities such as mono-ethoxylated, di-ethyoxylated choline, and ethylene glycol can form during this reaction and such impurities are often present in commercially available choline hydroxide.

SUMMARY

Improved processes for preparing choline hydroxide and the choline hydroxide produced by these processes are described. The processes involve feeding ethylene oxide, trimethylamine, and water into a first reactor to create a first reactor product. The first reactor temperature is maintained between 5° C. and 35° C. and the molar ratio of ethylene oxide to trimethylamine fed to the first reactor is equal to or less than one. The first reactor product is then fed into a second reactor to form a second reactor product. The second reactor is insulated, i.e., to allow for adiabatic heating in the second reactor. Finally, any unreacted trimethylamine is removed from the second reactor product to form a final product comprising choline hydroxide. The unreacted TMA that is removed from the second reactor product can be recycled and fed into the first reactor.

A further processes for preparing choline hydroxide using additional at least one additional reactor is also described. These processes involve feeding trimethylamine, water, and ethylene oxide into a first reactor to create a first reactor product. The first reactor temperature is maintained between 5° and 35° C. Next, the first reactor product and a second amount of ethylene oxide are fed into a second reactor to form a second reactor product. Like the first reactor, the second reactor temperature is maintained between 5° and 35° C. Then, the second reactor product is fed into a third reactor to form a third reactor product. The third reactor is insulated, i.e., to allow for adiabatic heating in the third reactor. Finally, any unreacted trimethylamine is removed from the third reactor product to form a final product comprising choline hydroxide. The unreacted TMA that is removed from the third reactor product can be recycled and fed into the first reactor.

DETAILED DESCRIPTION

Novel processes for preparing N,N,N-trimethylethanolammonium hydroxide (choline hydroxide) are described herein. These novel processes minimize the production of byproduct mono-ethoxylated and di-ethyoxylated choline in the product choline hydroxide. The processes generally include feeding ethylene oxide, trimethylamine, and water into a first reactor to create a first reactor product. The temperature of the first reactor is maintained between 5° and 35° C. and the molar ratio of ethylene oxide to trimethylamine fed to the first reactor is one to one or less than one to one (i.e., less ethylene oxide on a molar basis than trimethylamine). The product of the first reactor is fed into a second reactor to form a second reactor product. The second reactor is insulated allowing adiabatic heating. Finally, any unreacted trimethylamine in the second reactor product is removed to form a final product comprising choline hydroxide. Additional reactors can be used for the ethylene oxide and trimethylamine reaction.

The reaction chemistry of the processes as described herein is as follows:

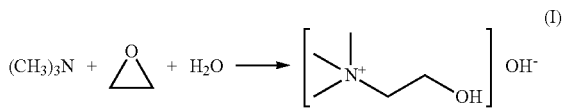

(I)

Specifically, trimethylamine (TMA), ethylene oxide (EO), and water react to form N,N,N-trimethylethanolammonium hydroxide (choline hydroxide) (see reaction scheme I). However, additional reactions utilizing the reactants available in the system are possible that create byproducts such as mono-ethoxylated choline (see reaction scheme II), di-ethyoxylated choline (see reaction scheme III), and ethylene glycol (see reaction scheme IV):

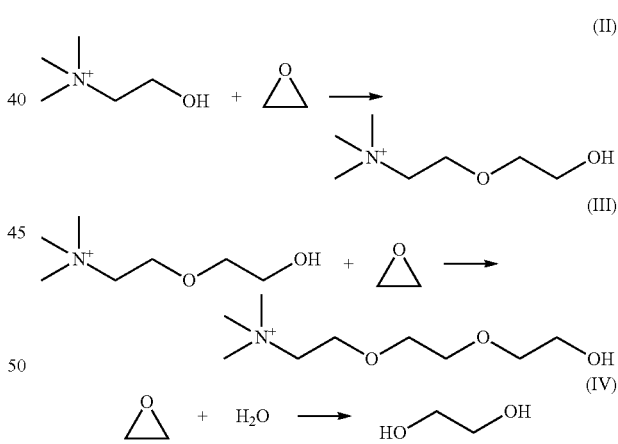

The processes described herein are designed to minimize the production of byproducts as illustrated by reaction schemes II, III, and IV.

Without being bound by theory, it is believed that these byproducts are generated in the reaction system when excess ethylene oxide is available. Specifically, any ethylene oxide not reacting with trimethylamine that comes into contact with choline hydroxide product can react to form the unwanted byproducts mono-ethoxylated and di-ethyoxylated choline. The processes described herein were designed to minimize the amount of ethylene oxide present in the reactors to an amount that will quickly react with available trimethylamine, such that excess ethylene oxide will not be available to react with choline hydroxide. The processes described herein are capable of providing choline hydroxide as a final product that is less than 10 weight percent mono-ethoxylated choline mono-ethoxylated and/or di-ethyoxylated choline. Additionally, a final choline hydroxide product can be produced using the methods described herein that is less than 9 weight percent, less than 8 weight percent, less than 7 weight percent, less than 6 weight percent, less than 5 weight percent, or less than 4 weight percent mono-ethoxylated choline mono-ethoxylated and/or di-ethyoxylated choline.

Figure 1:
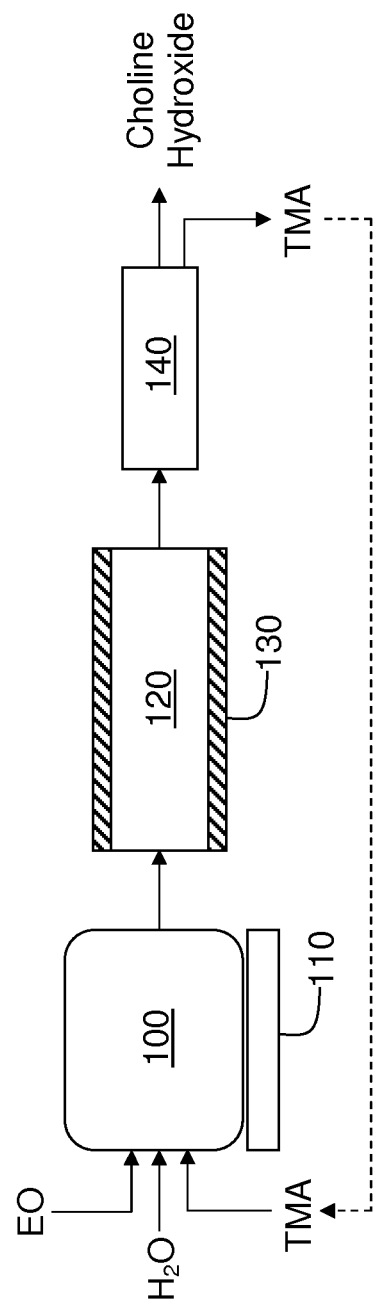
FIG. 1 shows a process for preparing choline hydroxide using two reactors and a TMA removal column.

A process as described herein for preparing choline hydroxide is shown in FIG. 1. The process includes feeding ethylene oxide (EO), trimethylamine (TMA), and water ($H_2O$) into a first reactor 100 to create a first reactor product. The first reactor temperature is maintained between 5° and 35° C. (e.g., by a temperature controller 110 at 20° C.) and the molar ratio of ethylene oxide to trimethylamine fed to the first reactor is equal to or less than one. Next, the first reactor product is fed into a second reactor 120 to form a second reactor product. The second reactor 120 is insulated (e.g., by an insulating material 130) which allows the second reactor 120 to retain the effect of adiabatic heating. Finally, any unreacted trimethylamine is removed from the second reactor product (e.g., using a column packed with a material capable of retaining trimethylamine) (shown diagrammatically as an apparatus 140) to form a final product comprising choline hydroxide. Optionally, the unreacted trimethylamine removed from the second reactor product can be recycled by feeding the unreacted trimethylamine back to the first reactor 100 through a suitable feed system (shown diagrammatically as a dashed line leading from the recycled unreacted TMA removed by apparatus 140 to the input TMA).

The reactants used in the processes described herein, i.e., ethylene oxide, trimethylamine, and water, are readily available from commercial sources and are easily selected and handled by those of skill in the art. As noted in reaction scheme I, the stoichiometric ratio of ethylene oxide to trimethylamine usage in the processes described herein is 1:1. Also as noted above, the availability of excess ethylene oxide in the reaction system is believed to be responsible for byproduct formation. For this reason, the processes described herein can operate at a maximum ratio of ethylene oxide to trimethylamine of 1:1. To help create a system in which excess ethylene oxide is not available a ratio of less than 1:1 (ethylene oxide to trimethylamine) can be used, i.e., 0.7:1, 0.75:1, 0.8:1, 0.85:1, 0.9:1, 0.92:1, 0.94:1, 0.95:1, 0.96:1, 0.97:1, 0.98:1, or 0.99:1. In some cases a slight excess of ethylene oxide may be used, for example when reaction conditions are optimized (e.g., 1.1:1, 1.09:1, 1.08:1, 1.07:1, 1.06:1, 1.05:1, 1.04:1, 1.03:1, 1.02:1, or 1.01:1)

The processes as described herein can be implemented using reactor systems for the first reactor that are well known to those of skill in the art. One type of reactor that can be used with the processes as described herein is a continuously stirred tank reactor. Another type of reactor that can be used with the processes as described herein is a loop reactor. A further type of reactor that can be used with the processes as described herein is a loop reactor with a high internal recycle ratio provided, for example, by a pump. The first reactor can be operated using batch or continuous modes of operation as will be apparent to those of skill in the art.

The processes as described herein can be implemented using reactor systems for the second reactor that also are well known to those of skill in the art. One type of reactor that can be used with the processes as described herein is a tube reactor. As used in the processes described herein, the second reactor is an insulated tube reactor.

In the processes described herein, the second reactor product is treated to remove any unreacted trimethylamine to provide the final choline hydroxide product. Methods and apparatus for removing trimethylamine from a choline hydroxide reaction product will be readily apparent to those of skill in the art. For example, unconverted trimethylamine can be stripped from the second reactor product using a distillation process, e.g., in a packed column using heated nitrogen. For further example, unconverted trimethylamine can be stripped from the second reactor product using one or more flash distillation units to remove the unconverted trimethylamine. As noted above, this unconverted trimethylamine can be recycled within the reactor system by adding it to the trimethylamine being fed into the reactor system. Additionally, the second reactor product or final product can be purified to remove unwanted byproducts such as, for example, mono-ethoxylated choline, di-ethyoxylated choline, and/or ethylene glycol. Such purification can be performed, for example, by distillation or other purification techniques that are well known to those of skill in the art.

Several factors have been found to impact the production of the unwanted byproducts mono-ethoxylated and di-ethyoxylated choline. First, the order in which the components are combined impacts both choline hydroxide and byproduct realization rates. Specifically, the addition of ethylene oxide to trimethylamine provides for fewer unwanted byproducts. Second, controlling the reaction temperature showed an increased choline hydroxide realization rate. Finally, the continuous (as opposed to batch) addition of ethylene oxide provides increased amounts of choline hydroxide in the final product when compared to the batch addition of ethylene oxide.

The addition of ethylene oxide to trimethylamine provides for fewer unwanted byproducts. As noted above, excess ethylene oxide is believed to increase the production of unwanted byproducts, so adding ethylene oxide to trimethylamine limits the amount of ethylene oxide available for producing byproducts.

Controlling the reaction temperature in various phases of the reaction can be used to reduce the variety and quantity of byproducts produced. For example, maintaining the reaction temperature between 5° C. and 35° C. when ethylene oxide, trimethylamine, and water are mixed can provide for fewer byproducts. Examples of temperature ranges useful for when ethylene oxide, trimethylamine, and water are mixed include maintaining the reaction temperature between 5° C. and 30° C., 5° C. and 25° C., 5° C. and 20° C., 5° C. and 15° C., 5° C. and 10° C., 10° C. and 35° C., 10° C. and 30° C., 10° C. and 25° C., 10° C. and 20° C., 10° C. and 15° C., 15° C. and 35° C., 15° C. and 30° C., 15° C. and 25° C., 15° C. and 20° C., 20° C. and 35° C., 20° C. and 30° C., and 20° C. and 25° C. A further example of a useful temperature for maintaining the reactor when ethylene oxide, trimethylamine, and water are mixed is 20° C.

Additionally, insulating the second reactor so that adiabatic heat is allowed to raise the temperature of the reactants can reduce the variety and quantity of byproducts produced. For example, adiabatic heating can raise the temperature in the second reactor product to between 15° and 45° C. Further examples of temperature ranges to which adiabatic heating can raise the temperature in the second reactor product include between 15° and 45° C., 15° and 40° C., 15° and 35° C., 15° and 30° C., 15° and 25° C., 15° and 20° C., 20° and 45° C., 20° and 40° C., 20° and 35° C., 20° and 30° C., 20° and 25° C., 25° and 45° C., 25° and 40° C., 25° and 35° C., 25° and 30° C., 30° and 45° C., 30° and 40° C., 30° and 35° C., 35° and 45° C., and 35° and 40° C. A further example of a temperature to which adiabatic heat is allowed to raise the temperature of the reactants in the second reactor is 40° C.

Continuous addition of ethylene oxide to trimethylamine present in a reactor provides for the lowest byproduct production when compared to batch addition of ethylene oxide. As will be apparent to those of skill in the art, ethylene oxide can be added to trimethylamine already present in a reactor or trimethylamine can be added to a reactor in a complimentary molar ratio simultaneously with the ethylene oxide to accomplish the same goal of limiting the amount of excess ethylene oxide available to form byproducts.

Additional reactors can also be used in the processes described herein. For example, an additional reactor similar to the first reactor can be added to the system between the two reactors already discussed. This additional reactor can be set up similar to the first reactor as discussed above, e.g., a temperature controlled loop reactor.

Figure 2:
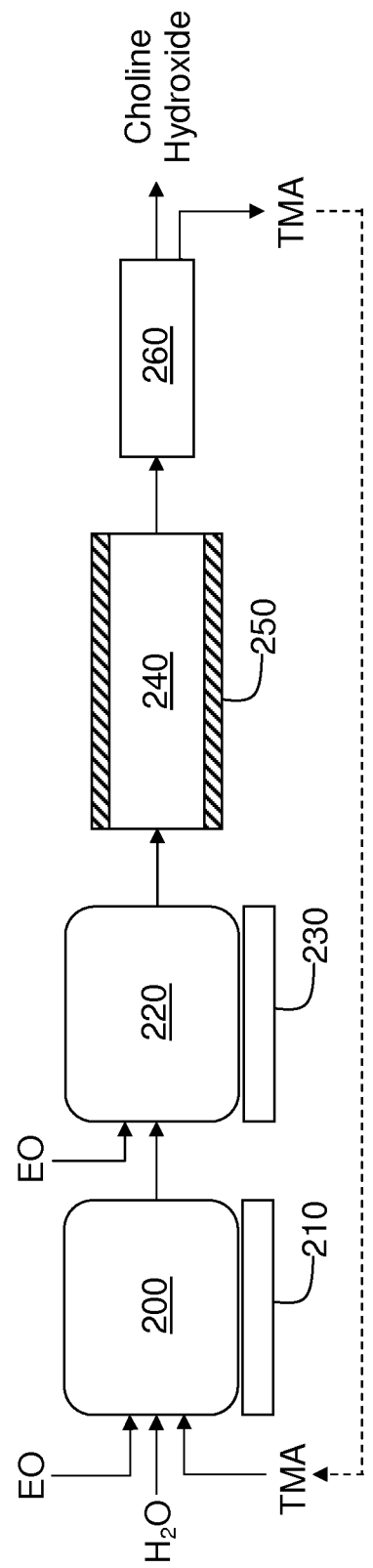
FIG. 2 shows a process for preparing choline hydroxide using three reactors and a TMA removal column.

If additional reactors are used, the ethylene oxide stream can be split such that a first portion of ethylene oxide goes to the first reactor and a second portion of ethylene oxide goes to the second reactor. The proportion of ethylene oxide directed to the first and second reactors can be, for example, between 50:50 and 99:1. Additional examples, of proportions of ethylene oxide directed to the first and second reactors can be, for example, between 60:40 and 99:1, 70:30 and 99:1, 75:25 and 99:1, 80:20 and 99:1, 85:15 and 99:1, 90:10 and 99:1, 92:8 and 99:1, 94:6 and 99:1, 95:5 and 99:1, 96:4 and 99:1, 97:3 and 99:1, and 98:2 and 99:1. FIG. 2 shows includes feeding ethylene oxide (EO), trimethylamine (TMA), and water ($H_2O$) into a first reactor 200 to create a first reactor product. The first reactor temperature is maintained between 5° and 35° C. (e.g., by a temperature controller 210 at 20° C.). Next, the first reactor product and an additional amount of ethylene oxide is fed into a second reactor 220 to form a second reactor product (the ethylene oxide could be added as a split stream between the first and second reactors as described above, but is only shown in FIG. 2 as separate feeds into each of the first and second reactors). The second reactor also is temperature controlled to between 5° and 35° C. (e.g., by a temperature controller 230 at 20° C.). Then the second reactor product is fed into a third reactor 240 to form a third reactor product. The third reactor 240 is insulated (e.g., by an insulating material 250) which allows the third reactor 240 to retain the effect of adiabatic heating. Finally, any unreacted trimethylamine is removed from the third reactor product (e.g., using a column packed with a material capable of retaining trimethylamine) (shown diagrammatically as an apparatus 260) to form a final product comprising choline hydroxide. Optionally, the unreacted trimethylamine removed from the third reactor product can be recycled by feeding the unreacted trimethylamine back to the first reactor 200 through a suitable feed system (shown diagrammatically as a dashed line leading from the recycled unreacted TMA removed by apparatus 260 to the input TMA). The amount of ethylene oxide fed into the second reactor 220 can be split from the ethylene oxide fed into the first reactor 200. For example, 90% of the ethylene oxide can go to the first reactor 200 and 10% of the feed can be directed to the second reactor 220.

The choline hydroxide made by the processes described herein has minimal amounts of byproduct mono-ethoxylated and di-ethoxylated choline in the product.

The following Examples are presented to illustrate various aspects of the processes and methods described herein and should not be construed as limitations to the claims.

Reactor

A 1.8 liter stainless steel reactor (Büchi; Uster, Switzerland) was used for Examples 1a, 1b, 2a, 2b, and 3 as described below. The reactor temperature was controlled using an oil circulation jacket (Mettler—Toledo; Columbus, Ohio). A pressure gauge (Swagelok; Solon, Ohio), thermocouple (OMEGA Engineering, Inc.; Stamford, Conn.), and agitation system to keep the reactor contents well-mixed (Magnetic Drive BM 130; Büchi (Uster, Switzerland)) were used with the reactor. Additionally, a Raman immersion probe (RXN1 Kaiser Raman spectrometer equipped with a 785-nm Invictus laser; Kaiser Optical Systems, Inc. (Ann Arbor, Mich.)) was fitted to the reactor in order to continuously monitor reactants and products in real time. A sample cylinder was installed on the top of the reactor in order to feed one of the reactants in a continuous mode or as series of shots. The bottom of the reactor was fitted with a block valve to discharge the reactor or collect product samples.

Chemicals

The following chemicals are used for Examples 1a, 1b, 2a, 2b, and 3 as described below:

De-ionized Water (produced in-house)

Trimethylamine (Sigma Aldrich; St. Louis, Mo.)—Chemical grade (Lot #s BCBC6791 and BCBD6638)

Ethylene Oxide (Airgas Southwest (The Woodlands, Tex.))—High Purity

Nitrogen gas (produced in-house)—Plant N2 (<50 ppm water, <5 ppm oxygen)

Ion Chromatography

Reaction products were analyzed using ion exchange chromatography (IC) with suppressed conductivity detection. A Dionex ICS—Reagent-Free Ion Chromatography (RFIC) (Dionex Corp.; Sunnyvale, Calif.) system was used. The ICS-3000 system consisted of a DP Dual Pump module, EG Eluent Generator module and DC Detector/Chromatography module with a single temperature zone configuration. The EG was equipped with an EluGen EGC II methanesulfonic acid (MSA) cartridge for electrolytic production of MSA eluent. Chromeleon 6.8 chromatography management software (Dionex Corp.) was used for system control, peak integration and area analysis.

Samples were injected into a 50 μL loop using an AS40 auto-sampler. The loop was mounted onto one of the two 6-port injection valves in the ICS 3000 DC module. Chromatographic separation was achieved using an IonPac CS A (4×250 mm) separator column preceded by an IonPac CG A (4×50 mm) guard column. The column effluent was passed through a CSRS 300 self regenerating suppressor used in the recycle water mode prior to conductivity detection. Isocratic MSA pumped at 1.0 ml/min was used. The chromatographic conditions are listed in table below.

| | |
|---|---|
| Columns | Dionex IonPac CG 12A, 4 × 50 mm (P/N 046074); IonPac CS 12A, 4 × 250 mm (P/N 046073) |
| Eluent | Isocratic 12 mM MSA |
| Eluent Source | EGC II MSA |
| Flow Rate | 1.0 ml/min |
| Temperature | 30° C. (lower and upper compartments) |
| Injection volume | 50 μL |
| Detection | Suppressed conductivity, CSRS |
| Suppressor | CSRS 300, 4 mm used in recycle mode with 70 mA |
| System backpressure | ~2200 psi |
| Background | <1.0 μS |
| Run time | 40 min |

NMR Analysis

Reaction products were also analyzed using $^1H$ and $^{13}C$ NMR as follows.

$^1H$ NMR

The samples were analyzed neat in a 5-mm NMR tube. Standards were prepared and analyzed in $D_2O$+DSP (chemical shift references). The data were collected using a Varian INOVA 500-MHz NMR spectrometer (Agilent Technologies; Santa Clara, Calif.), corresponding $^{13}C$ frequency of 499.77 MHz. The data were acquired using 100 transients per data file, a 33.3-second pulse repetition delay, a spectral width of 10,000 Hz and a file size of 32 k data points.

$^{13}C$ NMR

The samples were prepared by adding approximately 2 g of DMSO-d6 to 1 g of sample in a 10-mm NMR tube. The data were collected using a JEOL Eclipse 400 MHz NMR spectrometer (JEOL USA, Inc.; Peabody, Mass.), corresponding $^{13}C$ frequency of 100.5 MHz. The data were acquired using gated $^1H$ decoupling, transients per data file, a 121.3 second pulse repetition delay, a spectral width of 25,200 Hz, and a file size of 32K data points.

Example 1a

Ethylene Oxide batch addition @ 5° C.

In Example 1a the reactor was loaded with 275.32 g water and 123.7 g of trimethylamine. Then the reactor contents were agitated at 300 RPM (revolutions per minute), and the reactor temperature was controlled at 5° C. The reactor was purged with nitrogen then the nitrogen pressure in the reactor was raised to greater than 3 bar (to help keep the reactants in the liquid phase). When the temperature of the water and trimethylamine reached steady state at 5° C., ethylene oxide was fed into the reactor using pressurized nitrogen in four batches. The amount of ethylene oxide added in each batch was 14.59 g, 27.13 g, 24.4 g, and 30.5 g respectively. The agitation speed was increased to 400 RPM before the third batch of ethylene oxide was fed into the reactor. After the final batch of ethylene oxide was added, the reactor was purged with nitrogen for over 20 minutes before discharging the reaction product from the block valve located at the bottom of the reactor.

Product analysis using ion chromatography and NMR showed 44.1 wt % choline hydroxide, 6.2 wt % mono-ethoxylated byproduct, and the remainder was water.

Example 1b

Ethylene Oxide batch addition @ 25° C.

In Example 1b, the reactor was loaded with 261.83 g water and 118.52 g of trimethylamine. Then the reactor contents were agitated at 300 RPM, and the reactor temperature was controlled at 25° C. The reactor was purged with nitrogen then the nitrogen pressure in the reactor was raised to greater than 3 bar (to help keep most of the reactants in the liquid phase). When the temperature of the water and trimethylamine reached steady state at 25° C., ethylene oxide was fed into the reactor using pressurized nitrogen in four batches. The amount of ethylene oxide added in each batch was 14.13 g, 19.49 g, 25.76 g, and 37.39 g respectively. The agitation speed was increased to 400 RPM before the third batch of ethylene oxide was fed into the reactor. After the final batch of ethylene oxide was added, the reactor was purged with nitrogen for over 20 minutes before discharging the reaction product from the block valve located at the bottom of the reactor.

Figure 3:
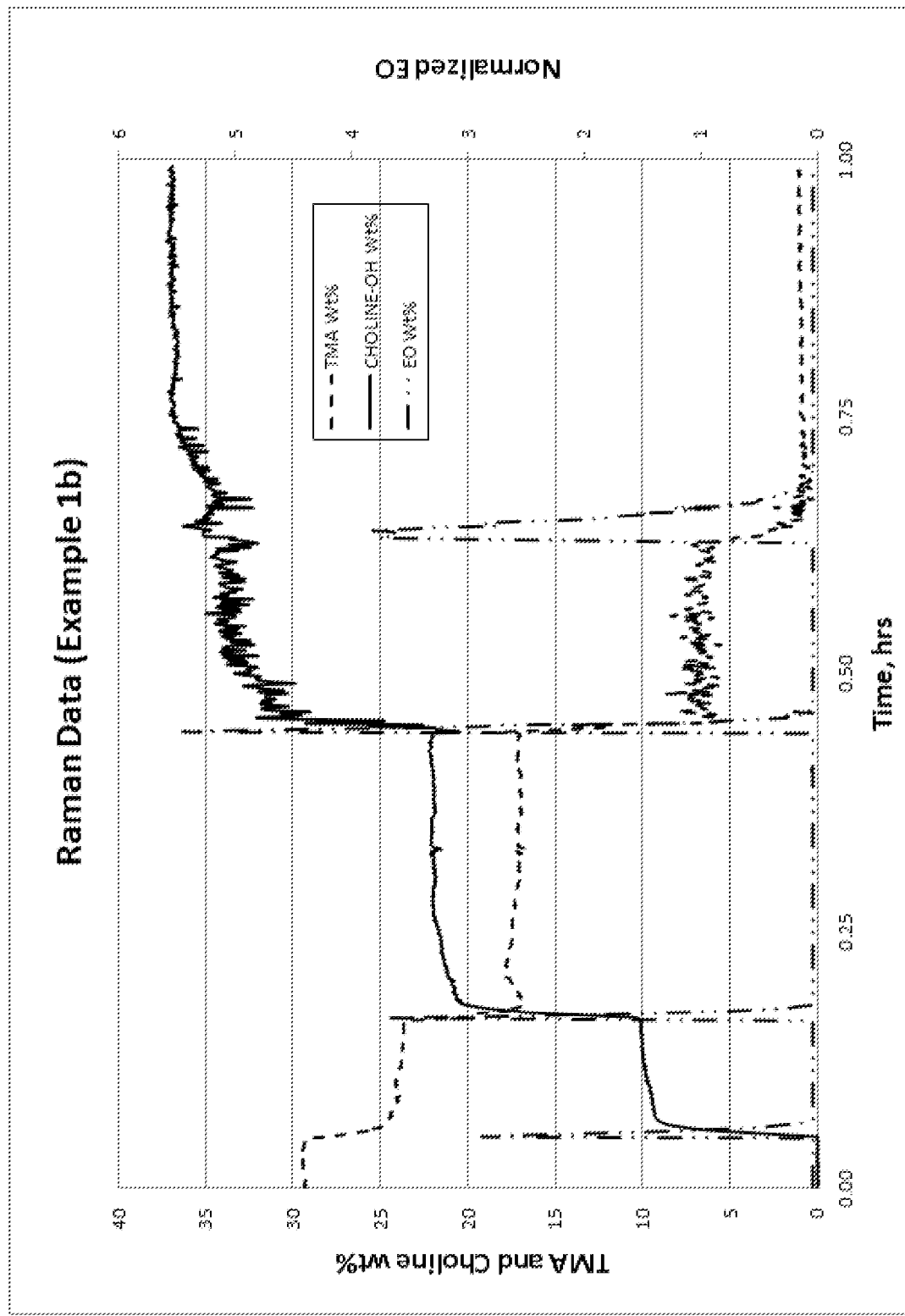
FIG. 3 is a Raman data plot showing the batch addition of ethylene oxide (EO 1273) to a reactor containing trimethylamine (TMA) and the production of choline hydroxide (cholineOH).

FIG. 3 is a Raman data plot showing the batch addition of ethylene oxide (EO 1273) to the reactor containing trimethylamine (TMA) and the production of choline hydroxide (cholineOH). The concentration of TMA decreases after each batch addition of ethylene oxide until no TMA is detected by the Raman probe after the fourth batch ethylene oxide addition and the amount of choline hydroxide product is headed toward its maximum.

Product analysis using ion chromatography and NMR showed 37.5 wt % choline hydroxide, 11.7 wt % mono-ethoxylated byproduct, and remainder was water.

Example 2a

Ethylene Oxide continuous addition @ 20° C.

In Example 2a, the reaction conditions were that same as in Example 1a except ethylene oxide was added in a continuous mode to the reactor containing 586.2 g water and 241.6 g trimethylamine and the reactor temperature was controlled at 20° C. The ethylene oxide addition rate was 4.95 g/min and ethylene oxide was added for 38.6 min.

Product analysis using ion chromatography and NMR showed 45.9 wt % choline hydroxide, 3.8 wt % mono-ethoxylated byproduct, and the remainder was water.

Example 2b

Ethylene Oxide continuous addition @ 25° C.

In Example 2b, the reaction conditions were the same as in Example 1a except ethylene oxide was added in a continuous mode to the reactor containing 249.52 g water and 112.61 g trimethylamine and the reactor temperature was controlled at 25° C. The ethylene oxide addition rate was 4.33 g/min and ethylene oxide was added for 20.6 minutes.

Product analysis using ion chromatography and NMR showed 44.4 wt % choline hydroxide, 6.0 wt % mono-ethoxylated byproduct, and the remainder was water.

Example 3

Trimethylamine Batch Addition @ 15° C.

In Example 3, the reaction conditions were the same as in Example 1a except trimethylamine was added batch-wise to the reactor (rather than ethylene oxide being added) and the reactor temperature was controlled at 15° C. The reactor contained a mixture of 144.78 g ethylene oxide and 182.02 g water. Trimethylamine added in two batches of 28.09 g and 38.25 g.

Product analysis using ion chromatography and NMR showed 11.9 wt % choline hydroxide, 17.2 wt % mono-ethoxylated byproduct, and the remainder was water.

Example 4

Recycling Excess TMA

The experimental results (Examples 1-3) were used to develop a kinetic model of the reaction system and the information was incorporated into a process model in ASPEN PLUS® (Aspen Technology, Inc.; Burlington, Mass.). The process was modified to include a distillation column for separating unconverted trimethylamine from the choline hydroxide reaction product and recycling the unconverted trimethylamine by feeding it back to the trimethylamine stream introduced into the first reactor. The recycling of unconverted trimethylamine enables lowering the feed of ethylene oxide relative to trimethylamine feed. The lowering of ethylene oxide to trimethylamine feed ratio (EO/TMA in feed to $1^{st}$ reactor) leads to higher yield of choline hydroxide and lowering of byproduct formation. As a consequence, the sizes for 1$^{st}$ and 3$^{rd}$ reactors can be decreased while maintaining the same process capacity. Lowering of EO/TMA ratio also significantly improved the overall raw material utilization. A typical result from the simulations is given below.

| Trimethylamine Recycle | No | Yes, 90% Recycle |
|---|---|---|
| 1$^{st}$ reactor residence time, min | 27.1 | 12.9 |
| 2$^{nd}$ reactor residence time, min | 6.1 | 6.1 |
| 3$^{rd}$ reactor residence time, min | 2.1 | 1.0 |
| Feed ratio of EO/TMA, kg/kg | 1.05 | 1.00 |
| TMA utilization, kg/kg | 90.6% | 96.2% |
| Choline hydroxide in the final product, weight fraction | 0.425 | 0.472 |
| Byproduct in the final product, weight fraction | 0.081 | 0.035 |

*TMA utilization is defined as one minus the mass flow ratio of the stripped-out TMA to the TMA feed.

Summary of the Examples

In the examples, several factors are notable. First, the order in which the components are combined impacts both choline hydroxide and byproduct realization rates. Specifically, when ethylene oxide is added to trimethylamine in Examples 1a, 1b, 2a, and 2b (as compared to Example 3), the choline hydroxide realization rate is much higher and byproduct production in lower. Second, controlling the reaction temperature showed an increased choline hydroxide realization rate. Specifically, in Examples 1a and 1b, the lower reaction temperature in Example 1a provided a greater percentage of choline hydroxide in the final product. Similarly, in Examples 2a and 2b, the lower temperature in Example 2a provided an increase in the percentage of choline hydroxide in the final product. Additionally, the continuous addition of ethylene oxide as in Examples 2a and 2b provided increased amounts of choline hydroxide in the final product as compared to the batch addition of ethylene oxide. Finally, in Example 4, modeling studies showed that recycling trimethylamine allows the ethylene oxide to trimethylamine feed ratio to be lowered providing other advantages in shorter reactor residence time, higher choline hydroxide weight fraction in the final product and lower byproduct levels.

The present invention is not limited in scope by the embodiments disclosed herein which are intended as illustrations of a few aspects of the invention and any embodiments which are functionally equivalent are within the scope of this invention. Various modifications of the processes, methods, and compositions in addition to those shown and described herein will become apparent to those skilled in the art and are intended to fall within the scope of the appended claims. Further, while only certain representative combinations of the process and method steps and composition components disclosed herein are specifically discussed in the embodiments above, other combinations of the composition components and process and method steps will become apparent to those skilled in the art and also are intended to fall within the scope of the appended claims. Thus a combination of components or steps may be explicitly mentioned herein; however, other combinations of components and steps are included, even though not explicitly stated. The term "comprising" and variations thereof as used herein is used synonymously with the term "including" and variations thereof and are open, non-limiting terms.

What is claimed is:

1. A process for preparing choline hydroxide comprising: feeding ethylene oxide, trimethylamine, and water into a first reactor to create a first reactor product, wherein the first reactor temperature is maintained between 5° C. and 35° C. and the molar ratio of ethylene oxide to trimethylamine fed to the first reactor is equal to or less than one; feeding the first reactor product into a second reactor to form a second reactor product, wherein the second reactor is insulated; and removing any unreacted trimethylamine from the second reactor product to form a final product comprising choline hydroxide.

2. The process of claim 1, wherein the choline hydroxide final product comprises less than 10 weight percent mono-ethoxylated choline and/or di-ethyoxylated choline.

3. The process of claim 1, wherein the trimethylamine and water are fed into the first reactor as a mixture.

4. The process of claim 1, wherein the residence time in the second reactor is sufficient for any unreacted ethylene oxide present in the first reactor product to react.

5. The process of claim 1, wherein adiabatic heating in the second reactor raises the temperature of the second reactor product to between 15° and 45° C.

6. The process of claim 1, wherein the first reactor is a continuously stirred tank reactor.

7. The process of claim 1, wherein the first reactor is a loop reactor with a high internal recycle ratio provided by a pump.

8. The process of claim 1, wherein the first reactor is maintained at 20° C.

9. The process of claim 1, wherein the unreacted trimethylamine is added to the trimethylamine fed into the first reactor.

10. A process for preparing choline hydroxide comprising: feeding trimethylamine, water, and ethylene oxide into a first reactor to create a first reactor product, wherein the first reactor temperature is maintained between 5° and 35° C.; feeding the first reactor product and a second amount of ethylene oxide into a second reactor to form a second reactor product, wherein the second reactor temperature is maintained between 5° and 35° C.; feeding the second reactor product into a third reactor to form a third reactor product, wherein the third reactor is insulated; and removing any unreacted trimethylamine from the third reactor product to form a final product comprising choline hydroxide.

11. The process of claim 10, wherein the choline hydroxide final product comprises less than 10 weight percent mono-ethoxylated choline and/or di-ethyoxylated choline.

12. The process of claim 10, wherein the trimethylamine and water are fed into the first reactor as a mixture.

13. The process of claim 10, wherein the residence time in the third reactor is sufficient for any unreacted ethylene oxide present in the second reactor product to react.

14. The process of claim 10, wherein adiabatic heating in the third reactor raises the temperature of the third reactor product to between 15° and 45° C.

15. The process of claim 10, wherein the second amount of ethylene oxide fed into the second reactor is split from the ethylene oxide fed into the first reactor.

16. The process of claim 10, wherein the ratio of amount of ethylene oxide fed into the first reactor to the second amount of ethylene oxide fed into the second reactor is between 50:50 and 99:1.

17. The process of claim 10, wherein the ratio of amount of ethylene oxide fed into the first reactor to the second amount of ethylene oxide fed into the second reactor is 90:10.

18. The process of claim 10, wherein the first reactor and second reactor are continuously stirred tank reactors.

19. The process of claim 10, wherein the first reactor and second reactor are loop reactors with high internal recycle ratios provided by a pump.

20. The process of claim 10, wherein the first reactor and second reactor are maintained at 20° C.

21. The process of claim 10, wherein the unreacted trimethylamine is added to the trimethylamine fed into the first reactor.

22. The method of claim 1, wherein the second reactor allows for uncontrolled adiabatic heating.

* * * * *